(12) United States Patent
Zobel (10) Patent No.: US 8,403,826 B1
(45) Date of Patent: Mar. 26, 2013

(54) VIDEO ENDOSCOPE FOR DIAGNOSTIC AND THERAPEUTIC USAGE

(75) Inventor: Jurgen Zobel, Pembroke Pines, FL (US)

(73) Assignee: Integrated Medical Systems International, Inc, Birmingham, AL (US)

( * ) Notice: Subject to any disclaimer, the term of this patent is extended or adjusted under 35 U.S.C. 154(b) by 419 days.

(21) Appl. No.: 12/706,851

(22) Filed: Feb. 17, 2010

Related U.S. Application Data (60) Provisional application No. 61/153,503, filed on Feb. 18, 2009.

(51) Int. Cl.
*A61B 1/04* (2006.01)
*A61B 1/06* (2006.01)
(52) U.S. Cl. .................................... 600/109; 600/173
(58) Field of Classification Search ............... 600/109, 600/112, 173
See application file for complete search history.

(56) References Cited

U.S. PATENT DOCUMENTS

| | | | | |
|---|---|---|---|---|
| 5,782,752 A | * | 7/1998 | Lichtman et al. | 600/137 |
| 6,277,064 B1 | * | 8/2001 | Yoon | 600/114 |
| 6,736,773 B2 | * | 5/2004 | Wendlandt et al. | 600/173 |
| 7,621,869 B2 | * | 11/2009 | Ratnakar | 600/173 |
| 8,096,941 B2 | * | 1/2012 | Fowler et al. | 600/102 |
| 2006/0149129 A1 | * | 7/2006 | Watts et al. | 600/113 |
| 2008/0021271 A1 | * | 1/2008 | Pasero et al. | 600/109 |
| 2009/0259097 A1 | * | 10/2009 | Thompson | 600/109 |

* cited by examiner

*Primary Examiner* — W. B. Perkey
(74) *Attorney, Agent, or Firm* — C. Brandon Browning; Maynard Cooper & Gale, PC

(57) ABSTRACT

A video endoscope for diagnostic and therapeutic usage including a rigid or flexible tube defining an axis and a compact video module arranged at a distal end of the tube along the axis, the video unit being configured to pivot off the axis for providing improved access of medical instruments through the distal end of the tube.

25 Claims, 6 Drawing Sheets

VIDEO ENDOSCOPE FOR DIAGNOSTIC AND THERAPEUTIC USAGE

This application claims priority to U.S. Provisional Patent Application No. 61/153,503, filed on Feb. 18, 2009 entitled VIDEO ENDOSCOPE FOR DIAGNOSTIC AND THERAPEUTIC USAGE, the entire contents of which are incorporated herein by reference.

FIELD OF INVENTION

This invention relates to a video endoscope for diagnostic and therapeutic usage. More particularly, the invention relates to a video endoscope including a rigid or flexible tube defining an axis and a compact video unit arranged at a distal end of the tube along or about the axis, the video unit being configured to pivot off the axis for providing improved access of medical instruments through the distal end.

BACKGROUND OF INVENTION

In the medical field endo scopes are used to enter the body along natural path ways. However, when there is no natural pathway, an incision is surgically created and a guiding tube called trocar or shaft is introduced. An endoscope is then inserted inside the body through the guiding tube. Incisions for receiving endoscopes are much less severe than openings required for open surgery. In the past when an endoscopic diagnostic was achieved and a surgical procedure deemed necessary, an open surgery was performed. Despite the open surgery, the endoscopic diagnostic preparing or evaluating the need of surgery was already an improvement regarding medical procedure and patient comfort.

For decades such endoscopes were used for diagnostic purposes only. These endoscopes were rigid or flexible endoscopes. Rigid endoscopes contain a lens system, and flexible endoscopes use glass fiber image bundles. The cross section of such endoscopes was divided between the illumination system and the imaging system only.

When optical performance of endoscopes improved significantly in the sixties and seventies, special endoscopes were made available to enable therapeutic procedures. These endoscopes have large rigid or flexible cylindrical tubes along the endoscope axis reserved solely for introducing instruments from the proximal side of the tubes into a patient's body through a distal end of the tube. Such instruments are large hand held mechanical instruments. Since the tubes are large, large incisions were needed. Larger incisions however result in a higher risk of infections and a longer healing process. Rarely incisions larger than for the use of 10 mm endoscopes are used. Now the cross section of an endoscope 10 mm or smaller in diameter had to be divided between the optical system containing illumination and imaging system and the instrument channel. So the introduction of such instrument channels in endoscopes reduces the cross section available for illumination fibers and imaging systems. Even with modern rod lens systems optical performance had to be compromised.

If the compromise on the optical performance for a specific application was too extreme, an endoscope without instrument channel was used and the instruments were inserted in the body through one or more additional incisions. Such additional incisions increase the risk of infection and extend the healing process. In rigid and flexible endoscopes for decades operating scopes with one or more channels for instruments or irrigation were compromises between a large channel cross section for robust instruments, strong flow of fluid or a powerful imaging system.

Since the nineties so-called video endoscopes came on the market. In video endoscopes the video chip is situated together with an objective system at the tip of the endoscope. Such combinations are used in rigid endoscopes and flexible endoscopes. Resolution of such chips has increased, signal processing improved and chips withstanding the high temperatures of the autoclave process were available.

Now more and more video endoscopes will replace rigid endoscopes with lens systems or flexible endoscopes with fiber image bundles. Such video endoscopes are having a compact unit at the tip. But along the length of the endoscope only a small portion of the cross section of the whole diameter is used for the electronic cables.

SUMMARY OF INVENTION

The present invention relates to flexible and rigid video endoscopes that are inserted through natural or surgically created openings in fairly large body cavities, e.g., laparoscopes and gastroscopes. The video endoscopes include an outer tube having a proximal end and a distal end and a compact module pivotably arranged about distal end of the outer tube. The compact module can include video imaging capabilities, illuminations capabilities or both. A pivot tube having a much smaller diameter than that of the compact module extends within the outer tube and operatively couples the compact module to the proximal end of the outer tube. The endoscope is configured so that after the compact module of the endoscope passes through the trocar or the natural pathway into a body cavity, the compact module can be moved off the center axis of the trocar or pathway by manipulating the pivot tube and locked in position to provide access for entry of surgical instruments through the outer tube into the body.

The compact module is moved off the center axis when inside the body cavity by rotating or pivoting the pivot tube thus rotating or pivoting the compact module sideways off the axis where it is locked in a position that allows a majority of the endoscope diameter to be used as an opening for guiding surgical instruments into the body cavity. After the surgical procedure is completed, the compact module can be unlocked, rotated or pivoted using the pivot tube back onto the axis and retracted into the outer tube, if applicable, before the endoscope is removed from the body cavity. When the compact unit includes a video chip, measures have to be taken to ensure the orientation of the chip in the observation position is correct after the compact module is rotated or pivoted out of the way.

The pivot tube operatively coupled to the much larger compact module may contain a cable for transferring signals between the compact module and the proximal end of the outer tube. These signals can include images collected by the compact module or electricity for powering the compact module. Further, the pivot tube can house illumination fibers which direct light into a body cavity through or around the compact module. Typically, the compact module will contain a video unit containing a video chip, an objective assembly and associated electronics inside of the chip housing. The compact module may also contain a source of illumination like a LCD or bulb.

Variations of the present invention are contemplated. For example, the endoscope can be modified to provide stereo endoscopes. That is, there can be left and right video modules, one for the left image and one for the right image wherein the modules are aligned side by side or consecutively for insertion purposes. In this variation, after the compact units enter the body cavity, they are rotated or pivoted side wards away from one another to give way for surgical instruments. The compact modules are positioned so that their optical axes converge at a desired distance and form a stereoscopic eye base between the left and right video cameras housed within the respective modules.

One benefit of the described endoscopes is that larger, stronger and more complex surgical instruments and optical systems can be accommodated by the endoscopes. Further, multiple surgical instruments, like needle holders and graspers, can be inserted through the endoscopes simultaneously.

DETAILED DESCRIPTION OF PREFERRED EMBODIMENT

FIGS. 1 through 16 depict preferred embodiments of endoscopes according to the present invention. In each embodiment, there is provided an outer endoscope tube for guiding medical instruments into a body cavity and at least one compact video module or illumination module extending there through and pivotably arranged about a distal end of the outer tube for providing improved access through the outer tube. A pivot tube is operatively coupled between the at least one compact module and a proximal end of the outer tube for containing transmission cables between the module and the proximal end. In use, the distal end of the pivot tube is manipulated to rotate or pivot the at least one module from within a pathway extending axially from the distal end of the outer tube to a position substantially adjacent to or outside of the pathway to provide improved access through and out of the distal end of the tube.

More particularly, the present invention is directed to a video endoscope that can be used for diagnostic purposes and as an operating scope. The main body of the endoscope is composed of a rigid or flexible insertion tube or outer tube. The majority of the cross section of the insertion tube is reserved for an inner tube or instrument tube through which surgical instruments can be inserted. A compact video module is pivotably mounted at the distal tip of the inserted endoscope. During insertion and retraction of the endoscope into a body cavity, the compact video module is coaxially positioned with the endoscope axis and sits in front of the instrument tube. After insertion, the video module can be moved in a way that the video module pivots or rotates side wards and gives way for the surgical instruments. Further, the video module can be moved such that the vertical axis of the video chip is aligned to provide an upright image and the optical axis is targeted to the object field.

Illumination can be built in the video module as a LED or bulb, or illumination can be provided through light guiding fibers aligned along the rigid or flexible endoscope between the inner instrument channel and the outer insertion tube. Other channels for air or fluid irrigation can be incorporated too. There can be also two compact video units which, for example, can be moved side wards and in the final position to provide a stereo endoscope with a right and a left video imaging capabilities.

The following examples are provided to further describe the features of the present invention.

Figure 1:
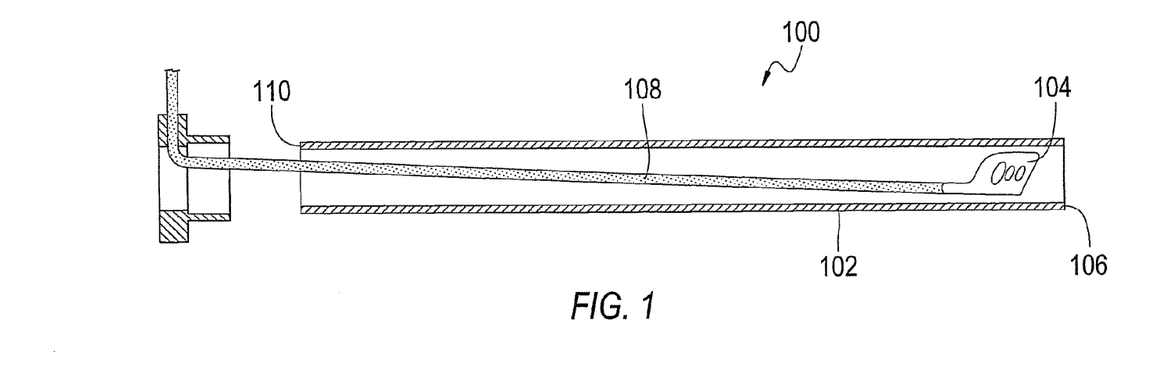
FIG. 1 is a sectional view of an endoscope including a pivotable video module with an integrated illumination unit in accordance with a preferred embodiment of the present invention. (4a).
Figure 2:
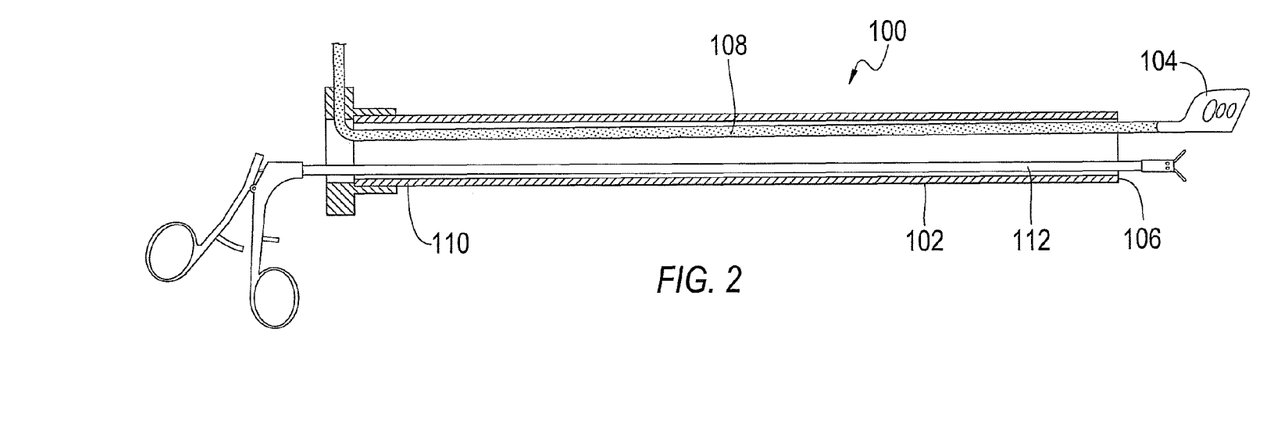
FIG. 2 is a sectional view of the endoscope of FIG. 1 including a medical instrument. (4b).

Referring to FIGS. 1 and 2, there is depicted an endoscope 100 including an outer insertion tube 102, a pivotable video module 104 having an integrated illumination unit and an integrated video unit, a distal end 106 and a bendable pivot tube 108 operatively coupled between video module 104 and a proximal end 110 of insertion tube. Pivot tube 108 contains video cables operatively coupled between video module 104 and a video monitor (not shown) on which images transmitted from video module 104 can be viewed.

In use, video module 104 is maintained within outer insertion 100 until distal 106 enters a body cavity. Thereafter, pivot tube 108 is moved in the direction of distal end 106 thereby moving video module 104 out of insertion tube 102. Once video module 104 is moved outside of insertion tube 102, pivot tube 108 is bent thus pivoting video module 104 sideward and substantially outside of a pathway defined by insertion tube 102 and a medical instrument 112 for providing access of instrument 112 through insertion tube 102 into the body cavity.

When insertion tube 102 is to be removed from inside of the body cavity, instrument 112 is retracted through proximal end 110 of insertion tube 102 and video module is pivoted back into the pathway defined by insertion tube 102. Video module 104 can then retracted back within insertion tube 102.

For the purpose of additional illumination or in place of the integrated illumination unit, light guiding fibers can be aligned inside pivot tube 108 and oriented towards the object field of the video unit of video module 104.

Figure 3:
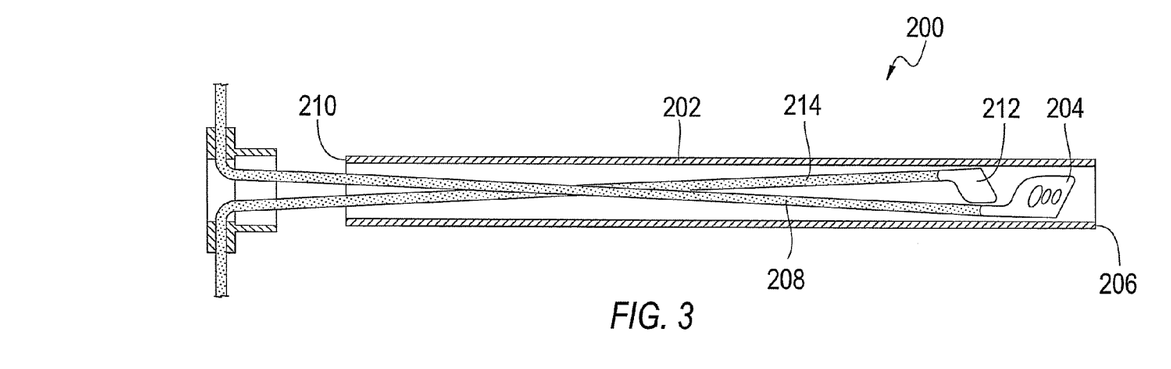
FIG. 3 is a sectional view of an endoscope including a pivotable video module and a pivotable illumination module in accordance with a preferred embodiment of the present invention. (6a)
Figures 4, 5:
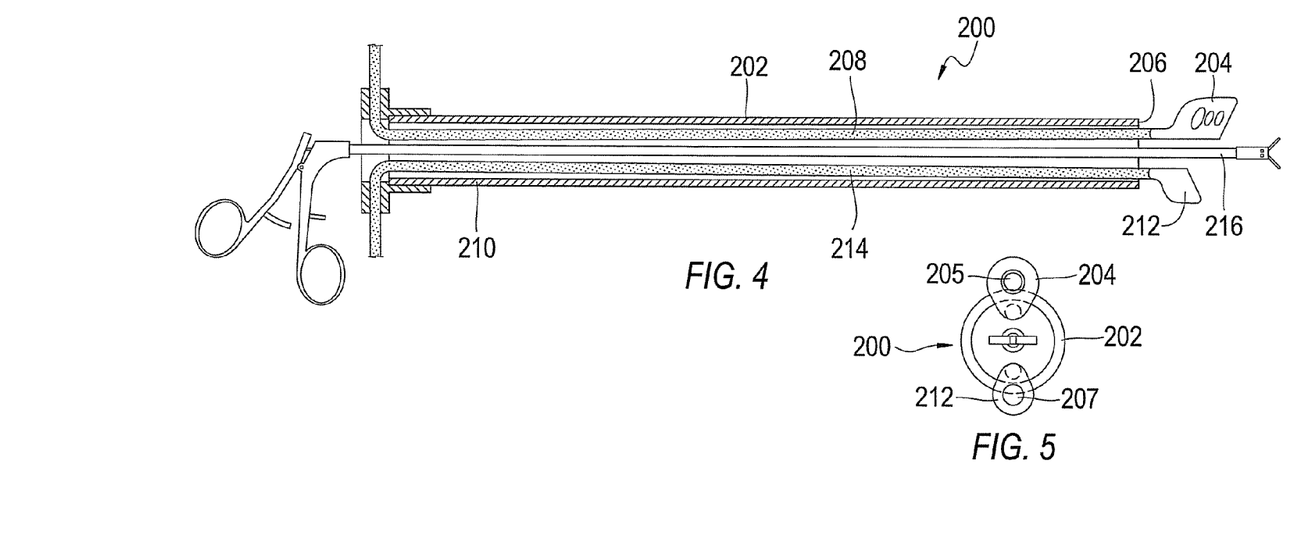
FIG. 4 is a sectional view of the endoscope of FIG. 3 including a medical instrument. (6b)
FIG. 5 is a plan view of the a distal end of the endoscope of FIG. 2. (6c)

Referring to FIGS. 3 through 5, there is depicted an endoscope 200 including an outer insertion tube 202, a pivotable video module 204 having an integrated video unit 205, a distal end 206, a bendable pivot tube 208 operatively coupled between video module 204 and a proximal end 210 of insertion tube, a pivotable illumination module 212 having an integrated illumination unit 207 and a bendable pivot tube 214 operatively coupled between video module 204 and a proximal end 210 of insertion tube 202. Pivot tube 208 contains video cables operatively coupled between video module 204 and a video monitor (not shown) on which images transmitted from video module 204 can be viewed. Pivot tube 214 includes wiring to operatively couple a power source for powering illumination module 212.

In use, video module 204 and illumination module 212 are contained within insertion tube 202 until distal end 206 of insertion tube 202 has entered a body cavity. Thereafter, video module 204 and illumination module 212 are moved out of insertion tube 202 through distal end 206 a pivoted sideward in different directions by bending pivot tubes 208 and 214, respectively. This opens a pathway through outer tube 202 through which a medical instrument 216 can be inserted into the body cavity. After the surgical procedure is finished, video module 204 and illumination module 212 are pivoted back within the pathway through outer tube 202 by bending pivot tubes 208 and 214, respectively. Modules 204 and 212 are then pulled back into insertion tube 202.

Figure 6:
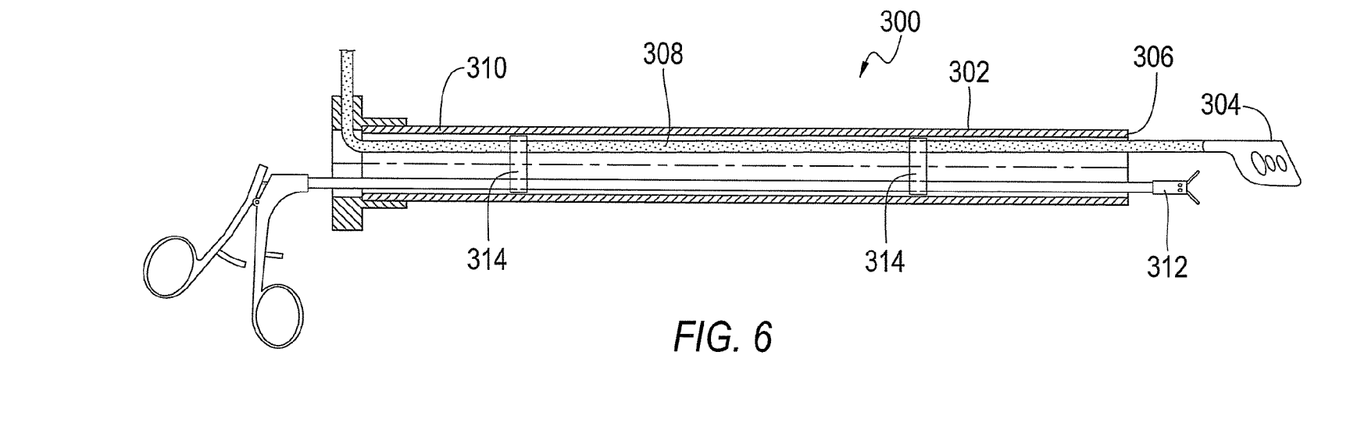
FIG. 6 is a sectional view of an endoscope including a pivotable video module with an integrated illumination unit and a medical instrument coupled thereto in accordance with a preferred embodiment of the present invention. (8a).
Figure 7:
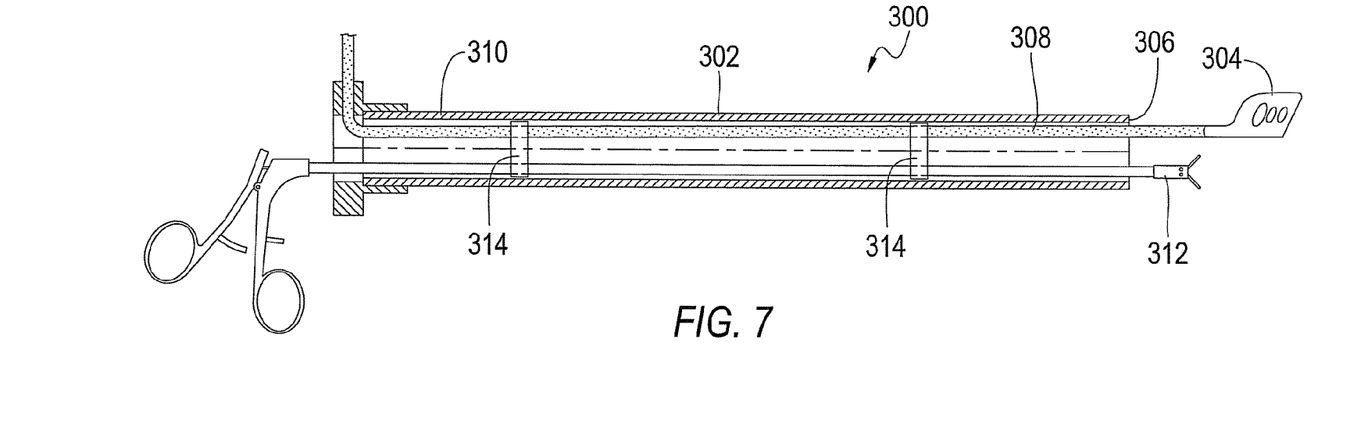
FIG. 7 is another sectional view of the endoscope of FIG. 6. (8b)

Referring to FIGS. 6 and 7, there is depicted an endoscope 300 including an outer insertion tube 302, a pivotable video module 304 having an integrated illumination unit and an integrated video unit, a distal end 306 and a bendable pivot tube 308 operatively coupled between video module 304 and a proximal end 310 of insertion tube. Pivot tube 308 contains video cables operatively coupled between video module 304 and a video monitor (not shown) on which images transmitted from video module 304 can be viewed. Endoscope 300 further includes a medical instrument 312 extending within outer tube 302 and coupled to pivot tube 308 using couplings 314. Video module 304 is situated in front of instrument 312 and coaxial therewith. Couplings 314 allow axial movement of instrument 312 relative to video module 304 and rotation of pivot tube 308.

In use, when video module 304 unit enters a body cavity, video module 304 unit is turned, tilted, shifted or bent sideward utilizing pivot tube 308 and locked in position out of the pathway of instrument 312. Instrument 312 can then be moved forward and backward in the field of view of the video module 304. Instrument 312 can be an applicator for a sterilization clip, a stapling device for suturing or any other endoscopic hand held instrument.

Figures 8, 9:
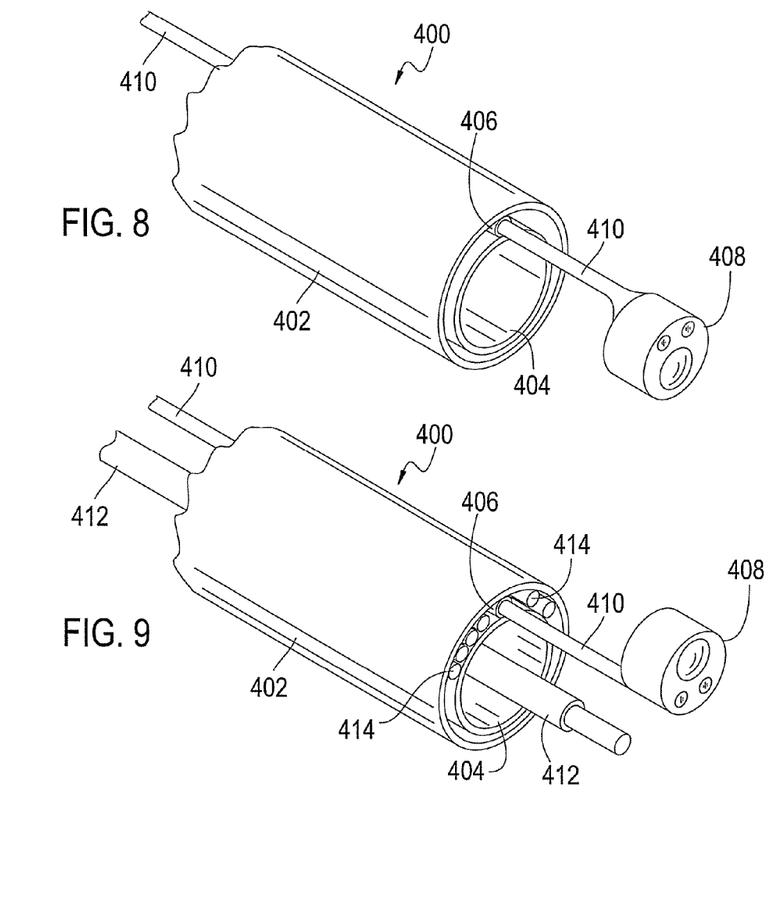
FIG. 8 is a perspective view of a distal end of an endoscope including a pivotable video module with an integrated illumination unit in accordance with another preferred embodiment of the present invention. (3a).
FIG. 9 is a perspective view of the distal end of the endoscope of FIG. 8 including a medical instrument. (3b—show dispersed illumination unit).

Referring to FIGS. 8 and 9, there is depicted an endoscope 400 including an outer insertion tube 402, an instruments tube 404 contained within insertion tube 402, a third tube 406 positioned between insertion tube 402 and instruments tube 404, a pivotable video module 408 having an integrated video unit and optionally an integrated illumination unit and a pivot tube 410 extending within third tube 406.

Instrument tube 404 is slightly smaller than insertion tube 402 and has an inside diameter that defines a pathway for the insertion of surgical instruments through insertion tube 402 and into a body cavity. Between these two tubes 402 and 404 is much smaller third tube 406. Inside third tube 406 is pivot tube 410. A distal end of pivot tube 410 is connected to video module 408. Through pivot tube 410 are cables for transferring video signals from video module 408 to a proximal end of insertion tube 402. At the proximal end a lever and a locking mechanism are connected to pivot tube 410. With turning the lever, pivot tube 410 is turned within third tube 406 and with that means video module 48 at the distal tip is turned. When video module 408 is turned around the axis of pivot tube 406, video module 408 is moved outside of or adjacent to the pathway defined by instrument tube 404 so that a medical instrument 412 can be pushed through and out of the distal end of insertion tube 402.

The direction of video module 408 is deflected so that in the outwards position, the video unit of video module 408 is directed at the inserted instrument 412 and site in the body cavity where instrument 412 is used. Thus, the chip in the video unit is oriented in a way that in the locked position the image orientation on the video monitor to which the video unit is coupled is in the desired position. During insertion and retraction of video module 408, the image orientation can be corrected by turning the module 408.

The space between insertion tube 402 and instrument tube 404 can be filled with illumination fibers 414 to increase lighting within the body cavity or in the event video module does not include an integrated illumination unit. Alternatively, the space can be filled with solder or glue.

Figures 10, 12:
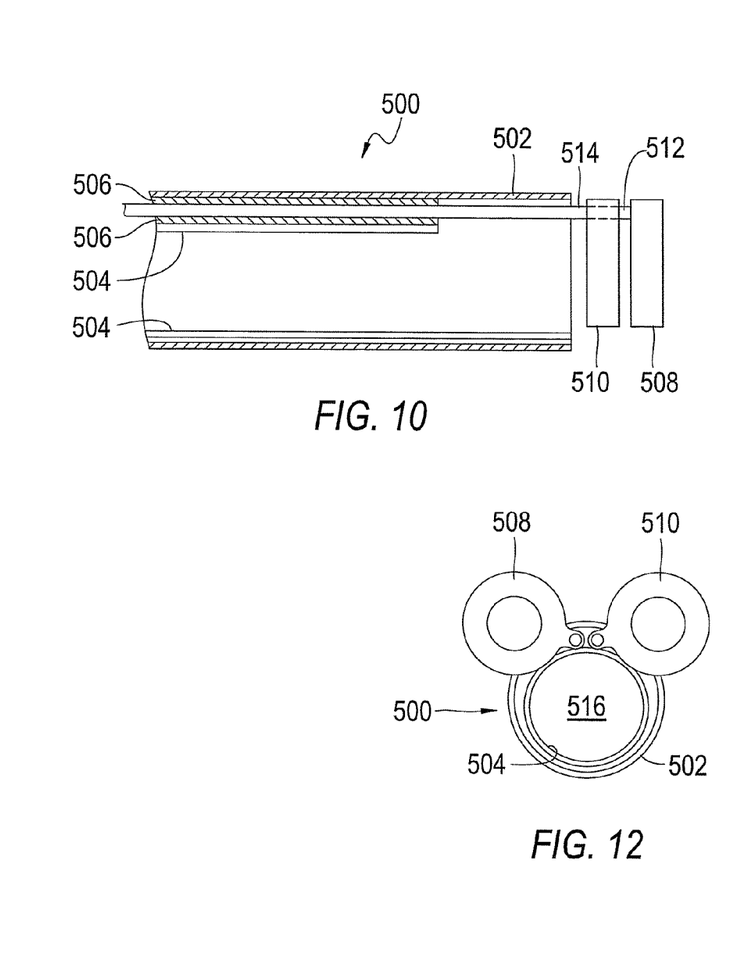
FIG. 10 is a sectional view of a distal end of an endoscope including a pivotable video module and a pivotable illumination module in accordance with a preferred embodiment of the present invention wherein the modules are arranged consecutively and pivot about respective parallel axes. (5a)
FIG. 12 is a plan view of the distal end of the FIG. 10 showing the modules pivoted apart. (5b).
Figure 11:
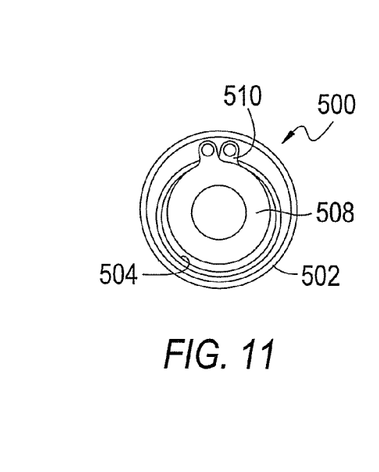
FIG. 11 is a plan view of the distal end of the endoscope of FIG. 10 showing the modules aligned. (5a)

Referring to FIGS. 10 through 12, there is depicted an endoscope 500 including an outer insertion tube 502, an instruments tube 504 contained within insertion tube 502, a third tube 506 positioned between insertion tube 502 and instruments tube 504, a pivotable video module 508 having an integrated video unit, a pivotable illumination module 510, a first pivot tube 512 extending within third tube 506 operatively coupled to video module 508 and a second pivot tube 514 extending within third tube 506 operatively coupled to illumination module 510. Video module 508 and illumination module 510 are arranged consecutively and pivot about respective parallel axes. As shown, video module 508 is arranged in front of illumination module 510 though their positions may be revered with video module 508 being positioned behind illumination module 510.

In use, with video module 508 and illumination module 510 arranged consecutively and withdrawn into a distal end of insertion tube 502, insertion tube 502 is inserted into a body cavity. After video module 508 and illumination module 510 enter the body cavity they are pushed forward into the body by pushing first pivot tube 512 and second pivot tube 514, respectively, toward the body cavity and then turned around parallel axes moving them to opposite sides of insertion tube 502 where they and locked in place by means located at the proximal end. In that position, an instrument channel 516 is opened up to allow for the introduction of medical instruments though insertion tube 502 into the body cavity. Illumination module 510 can be directed towards the object plane directly illuminating the object field or illumination module 510 can be spread in different directions using the wall of the body cavity to reflect the light back indirectly. When illumination module 510 is positioned in front of video module 508, the separation of the illumination location and video module 510 creates shadows and results in a more plastic appearance of the objects observed in the body cavity. Indirect illumination additionally enhances contrast and plasticity.

Figure 13:
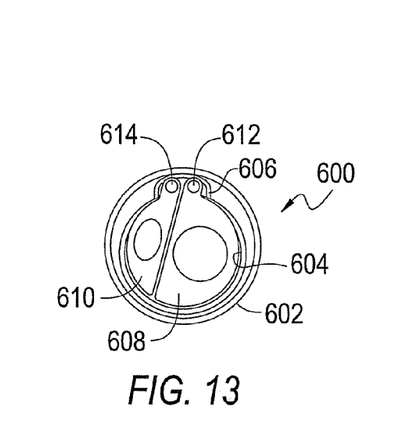
FIG. 13 is a plan view of a distal end of an endoscope including a pivotable video module and a pivotable illumination module in accordance with a preferred embodiment of the present invention wherein the modules are arranged side-by-side and pivot about respective parallel axes. (5a)
Figure 14:
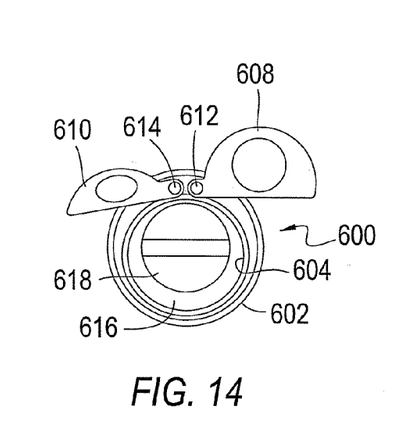
FIG. 14 is a plan view of the distal end of the FIG. 13 showing the modules pivoted apart. (5b).

Referring to FIGS. 13 and 14, there is depicted an endoscope 600 including an outer insertion tube 602, an instruments tube 604 contained within insertion tube 602, a third tube 606 positioned between insertion tube 602 and instruments tube 604, a pivotable video module 608 having an integrated video unit, a pivotable illumination module 610, a first pivot tube 612 extending within third tube 606 operatively coupled to video module 608 and a second pivot tube 614 extending within third tube 606 operatively coupled to illumination module 610. Video module 508 and illumination module 610 are arranged side-by-side and pivot about respective parallel axes.

In use, with video module 608 and illumination module 610 arranged side by side, insertion tube 602 is inserted into a body cavity. After video module 608 and illumination module 610 enter the body cavity they are turned around parallel axes moving them to opposite sides of insertion tube 602 where they and locked in place by means located at the proximal end. In that position, an instrument channel 616 is opened up to allow for the introduction of a medical instrument 618 though insertion tube 602 into the body cavity.

Figure 15:
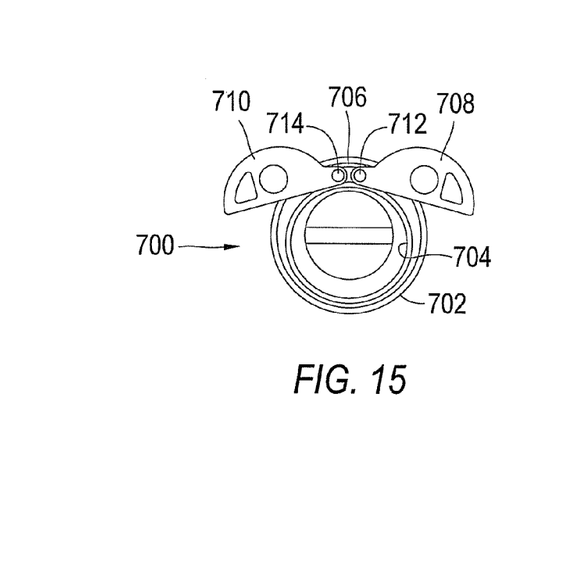
FIG. 15 is a plan view of a distal end of an endoscope including a right pivotable video module and a left pivotable video module in accordance with a preferred embodiment of the present invention wherein the modules are arranged side-by-side and pivot about respective parallel axes. (7b)

Referring to FIG. 15, there is depicted an endoscope 700 including an outer insertion tube 702, an instruments tube 704 contained within insertion tube 702, a third tube 706 positioned between insertion tube 702 and instruments tube 704, a pivotable right video module 708 having an integrated video unit, a pivotable left video module 710 having an integrated video unit, a first pivot tube 712 extending within third tube 706 operatively coupled to video module 708 and a second pivot tube 714 extending within third tube 706 operatively coupled to video module 710. Right video module 708 and left video module 710 are arranged side by side and pivot about respective parallel axes.

According to this arrangement, two video modules 708 and 710 are provided. When in use inside of a body cavity, the use of two video modules presents a left and right imaging system of a stereo endoscope for observing a surgical instrument 716 and enhancing the depth perception during the procedure. Illumination can be built in one or both of the video units or conventional illumination fibers can be assembled between insertion tube 702 and instrument tube 704.

Figure 16:
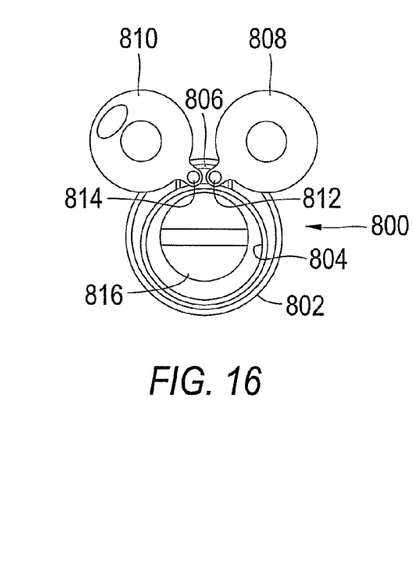
FIG. 16 is a sectional view of a distal end of an endoscope including a front pivotable video module and a back pivotable video module in accordance with a preferred embodiment of the present invention wherein the modules are arranged consecutively and pivot about respective parallel axes. (7b)

Referring to FIG. 16, there is depicted an endoscope 800 including an outer insertion tube 802, an instruments tube 804 contained within insertion tube 802, a third tube 806 positioned between insertion tube 802 and instruments tube 804, a pivotable front video module 808 having an integrated video unit, a pivotable back video module 810 having an integrated video unit, a first pivot tube 812 extending within third tube 806 operatively coupled to video module 808 and a second pivot tube 814 extending within third tube 806 operatively coupled to video module 810. Front video module 808 and back video module 810 are arranged consecutively and pivot about respective parallel axes.

According to this arrangement, two video modules 808 and 810 are provided. When in use inside of a body cavity, the use of two video modules presents a left and right imaging system of a stereo endoscope for observing a surgical instrument 816 and enhancing the depth perception during the procedure. Illumination can be built in one or both of the video units or conventional illumination fibers can be assembled between insertion tube 802 and instrument tube 804. Video modules 808 and 810 can be moved forward so that both video modules sit at the same longitudinal level but building a left and a right eye base. This arrangement has a much better stereoscopic effect than conventional stereo endoscopes.

One of many possible embodiments for flexible endoscopes according to the idea is a reinforced plastic tube as a guiding pass for the instruments where in the side wall a small flexible tube is embedded. Through the tube goes a flexible wire which is connected to a compact video unit at the tip of said reinforced plastic tube. Through a mechanical steering unit at the proximal end of said reinforced plastic tube the wire deflects the video unit at the distal tip until the video unit gives way for the flexible surgical instruments. The deflected video unit is under tension from the steering unit at the proximal end and hold in position by a pin Illumination can be built in the wall of said reinforced plastic tube or in the video unit as a LED or bulb.

As will be apparent to one skilled in the art, various modifications can be made within the scope of the aforesaid description. Such modifications being within the ability of one skilled in the art form a part of the present invention and are embraced by the claims below.

It is claimed:
1. An endoscope comprising,
a first tube having a proximal end and a distal end,
an imaging module pivotably arranged about the distal end of the first tube for receiving and transmitting images,
an image transmission member operatively coupled to the imaging module and extending within the first tube toward the proximal end for transmitting the images from the imaging module through the endoscope to a user,
an imaging module pivot member operatively coupled to the imaging module, extending within the first tube and configured for pivoting the imaging module between a first position and a second position, and
an illumination module that is separate from the imaging module and pivotably arranged about the distal end of the first tube.
2. The endoscope according to claim 1 wherein the first position includes the imaging module blocking access through a portion of an opening through the distal end of the first tube and the second position includes the imaging module allowing access through the portion of the opening.
3. The endoscope according to claim 1 wherein the first position includes the imaging module extending across an axis defined by the outer tube and the second position includes the imaging module off of the axis.
4. The endoscope according to claim 1 wherein the image transmission member is at least partially contained within the imaging module pivot member.
5. The endoscope according to claim 1 wherein the imaging module pivot member is coupled to a medical instrument extending through the first tube in manner such that axial movement of the medical instrument is translated to the imaging module.
6. The endoscope according to claim 1 further comprising a light transmission member operatively coupled to the illumination module and extending within the first tube toward the distal end, and an illumination module pivot member operatively coupled to the illumination module and configured for pivoting the illumination module between a third position and a fourth position.
7. The endoscope according to claim 6 wherein the third position includes the illumination module blocking access through a portion of an opening through the distal end of the first tube and the second position includes the illumination module allowing access through the portion of the opening.
8. The endoscope according to claim 1 wherein the imaging module is at least partially contained within the first tube.

9. The endoscope according to claim 1 further comprising a second tube contained within the first tube, the second tube containing the image transmission member and the imaging module pivot member wherein the second tube is not pivotable about the distal end of the first tube.

10. The endoscope according to claim 9 further comprising a third tube contained within the first tube wherein the second tube is located between the first tube and the third tube.

11. The endoscope according to claim 10 further comprising an illumination bundle located between the first tube and the third tube.

12. The endoscope according to claim 9 further comprising an illumination module pivotably coupled about the distal end of the first tube and a light transmission member operatively coupled to the illumination module and extending through the second tube toward the proximal end of the first tube.

13. The endoscope according to claim 12 further comprising an illumination module pivot member operatively coupled to the illumination module and configured for pivoting the illumination module between a third position and a fourth position wherein the third position includes the illumination module blocking access through a portion of an opening through the distal end of the first tube and the second position includes the illumination module allowing access through the portion of the opening.

14. The endoscope according to claim 12 wherein the illumination module pivot member is positioned between the video module and the distal end of the first tube.

15. The endoscope according to claim 12 wherein the illumination module is positioned beside the video module.

16. The endoscope according to claim 1 wherein the first position is substantially across a pathway defined by and extending axially through and out the distal end of the first tube and the second position is substantially adjacent to the pathway.

17. The endoscope according to claim 1 wherein the imaging module includes a first pivotable imaging unit and a second pivotable imaging unit.

18. The endoscope according to claim 17 wherein the first pivotable imaging unit is pivotable independent of the second pivotable imaging unit.

19. The endoscope according to claim 18 wherein each of the first pivotable imaging unit and the second pivotable imaging unit has a semi-circular cross-section.

20. An endoscope comprising,
an outer tube having a distal end and a proximal end,
an instrument tube contained within the outer tube configured for guiding medical instruments through the outer tube,
an imaging tube positioned between the outer tube and the instrument tube, the imaging tube having a first diameter that is less than that of the instrument tube and a distal end face that is recessed within the distal end of the outer tube,
a video module pivotably coupled with the imaging tube, the video module having a second diameter that is greater than the first diameter,
a video module pivot member operatively coupled to the video module and at least partially contained within the imaging tube, and
a video transmission member operatively coupled to the video module and extending toward the proximal end of the first tube.

21. The endoscope according to claim 20 wherein the first diameter is at least 75% less than that of the instrument tube.

22. The endoscope according to claim 21 wherein the second diameter is at least 200% greater than that of the first diameter.

23. The endoscope according to claim 20 wherein the video module is pivotable between a first position where it essentially prevents access of the medical instruments through the instrument tube and out through an opening in the distal end of the outer tube and a second position where it allows essentially full access of medical instruments through the instrument tube and out through the opening.

24. The endoscope according to claim 20 wherein the video module is selectively pivotable away from an axis of the outer tube.

25. The endoscope according to claim 21 wherein the video module includes a right imaging unit and a left imaging unit wherein the right imaging unit is pivotable independent of the left imaging unit.

* * * * *